US010287612B2

(12) United States Patent
Kawahara et al.

(10) Patent No.: US 10,287,612 B2
(45) Date of Patent: May 14, 2019

(54) MODIFIED CYANOBACTERIA

(71) Applicants: Kao Corporation, Chuo-ku, Tokyo (JP); Saitama University, Saitama-shi, Saitama (JP)

(72) Inventors: Akihito Kawahara, Wakayama (JP); Yukako Sonoike, Saitama (JP); Ayumi Kizawa, Saitama (JP)

(73) Assignees: Kao Corporation, Tokyo (JP); Saitama University, Saitama-shi, Saitama (JP)

(*) Notice: Subject to any disclaimer, the term of this patent is extended or adjusted under 35 U.S.C. 154(b) by 0 days.

(21) Appl. No.: 15/536,423

(22) PCT Filed: Dec. 21, 2015

(86) PCT No.: PCT/JP2015/085669
§ 371 (c)(1),
(2) Date: Jun. 15, 2017

(87) PCT Pub. No.: WO2016/104424
PCT Pub. Date: Jun. 30, 2016

(65) Prior Publication Data

US 2018/0163237 A1 Jun. 14, 2018

(30) Foreign Application Priority Data

Dec. 22, 2014 (JP) ................................ 2014-258493

(51) Int. Cl.

| | |
|---|---|
| ***C12P 7/64*** | (2006.01) |
| ***C07K 14/195*** | (2006.01) |
| ***C12N 1/20*** | (2006.01) |
| ***C12N 9/00*** | (2006.01) |
| ***C12N 15/10*** | (2006.01) |
| ***C12N 9/18*** | (2006.01) |
| ***C12N 15/09*** | (2006.01) |
| ***C12N 9/16*** | (2006.01) |

(52) U.S. Cl.
CPC .......... *C12P 7/6409* (2013.01); *C07K 14/195* (2013.01); *C12N 1/20* (2013.01); *C12N 9/16* (2013.01); *C12N 9/18* (2013.01); *C12N 9/93* (2013.01); *C12N 15/09* (2013.01); *C12N 15/102* (2013.01); *C12Y 301/02* (2013.01); *C12Y 301/02014* (2013.01); *C12Y 602/0102* (2013.01)

(58) Field of Classification Search
CPC .......... C07K 14/195; C12P 7/64; Y02E 50/13
See application file for complete search history.

(56) References Cited

U.S. PATENT DOCUMENTS

| | | | | |
|---|---|---|---|---|
| 8,980,613 | B2 * | 3/2015 | Roberts .................... | C12N 9/20 435/193 |
| 2009/0298143 | A1 | 12/2009 | Roessler et al. | |
| 2012/0237987 | A1 * | 9/2012 | Curtiss .................... | C12N 1/20 435/134 |

FOREIGN PATENT DOCUMENTS

| | | | |
|---|---|---|---|
| JP | 2011-229482 | A | 3/2011 |
| JP | 2011-505838 | A | 3/2011 |
| JP | 2015-142517 | A | 8/2015 |
| WO | WO 2009/076559 | A1 | 6/2009 |

OTHER PUBLICATIONS

Gutenkunst et al., LexA regulates the bidrectional hydrogenase in the cyanobacterium *Synechocystis* sp. PCC 6803 as a transcription activator. Mol. Microbiol., 2005, vol. 58(3): 810-823 (Year: 2005).*
Hackenberg et al., Low-carbon acclimation in carboxysome-less and photorespiratory mutants of the cyanobacterium *Synechocystis* sp. strain PCC 6803. Microbiol., 2012, vol. 158: 398-413. (Year: 2012).*
Kumar et al., LexA protein of cyanobacterium *Anabena* sp. strain PCC7120 exhibits in vitro pH-dependent and RecA-independent autoproteolytic activity. The Int. J. Biochem. Cell Biol., 2015, vol. 59: 84-93. (Year: 2015).*
Lleman-Hurwitz et al., A cyanobacterial AbrB-like protein affects the apparent photosynthetic affinity for CO2 by modulating low-CO2-induced gene expression. Environ. Microbiol. 2009, vol. 11(4): 927-936. (Year: 2009).*
Li et al., Computational analysis of LexA regulons in Cyanobacteria. BMC Genomics, 2010, vol. 11: 527, pp. 1-17. (Year: 2010).*
Oliveira et al., Novel insights into regulation of LexA in the cyanobacterium *Synechocystis* sp. Strain PCC 6803. J. Bacteriol., 2011, vol. 193(15): 3804-3814. (Year: 2011).*
International Search Report (ISR) for PCTIJP2015/085669; I.A. fd: Dec. 21, 2015, dated Mar. 29, 2016 from the Japan Patent Office, Tokyo, Japan.
International Preliminary Report on Patentability (IPRP), Chapter I of the Patent Cooperation Treaty, including the Written Opinion for PCT/JP2015/085669; I.A. fd: Dec. 21, 2015, dated Jun. 27, 2017, by the International Bureau of WIPO, Geneva, Switzerland.
Kamei, A et al., "Functional analysis of LexA-like gene sll1626 in *Synechocystis* sp. PCC 6803 using DNA microarray," Plant and Cell Physiology, 2001, 42(Supplement):s95, Japanese Society of Plant Physiologists, Oxford University Press, Tokyo, Japan.
Kamei, A el al., "Functional analysis of lexA-like gene, sl;1626 in *Synechocystis* sp. PCC 6803 using DNA 'microarray," in: Proceedings of the 12*th* International Congress, of Photosynthesis, No. S41-013 (four pages), Aug. 18-23, 2001, Brisbane, CSIRO Publishing, Melbourne, AU.
Yoshino, F et al, "High photobiological hydrogen production activity of a *Nostoc* sp. PCC 7422 uptake hydrogenase-deficient mutant with high nitrogenase activity," Mar Biotechnol (NY). Jan.-Feb. 2007;9(1):101-12. Epub Nov. 28, 2006, Springer-Verlag, NY.

(Continued)

*Primary Examiner* — Ganapathirama Raghu
(74) *Attorney, Agent, or Firm* — Sterne, Kessler, Goldstein & Fox, P.L.L.C.

(57) ABSTRACT

Provided is a cyanobacterium improved in fatty acid productivity. A method for producing a modified cyanobacterium, comprising causing loss of function of a LexA transcriptional regulator and acyl-ACP synthetase in a cyanobacterium.

19 Claims, 2 Drawing Sheets

Specification includes a Sequence Listing.

(56) References Cited

OTHER PUBLICATIONS

Deng, M-D et al., "Ethanol synthesis by genetic engineering in cyanobacteria," Appl Environ Microbiol. Feb. 1999;65(2):523-8, American Society for Microbiology, Washington, DC.

Atsumi, S et al., "Direct photosynthetic recycling of carbon dioxide to isobutyraldehyde," Nat Biotechnol. Dec. 2009;27(12): 1177-80. doi: 10.1038/nbt.1586, Nature America Publishing, NY.

Liu, X et al., "Fatty acid production in genetically modified cyanobacteria," Proc. Nati Acad Sci U S A. Apr. 26, 2011;108(17):6899-904. doi: 10.1073/pnas.1103014108. Epub Apr. 11, 2011, National Academy of Sciences, Washington, DC.

Domain, F et al., "Function and regulation of the cyanobacterial genes lexA , recA and ruvB: LexA is critical to the survival of cells facing inorganic carbon starvation," Mol Microbiol. Jul. 2004;53(1):65-80, Blackwell Scientific Publications, Oxford, England.

* cited by examiner

[Figure 1]
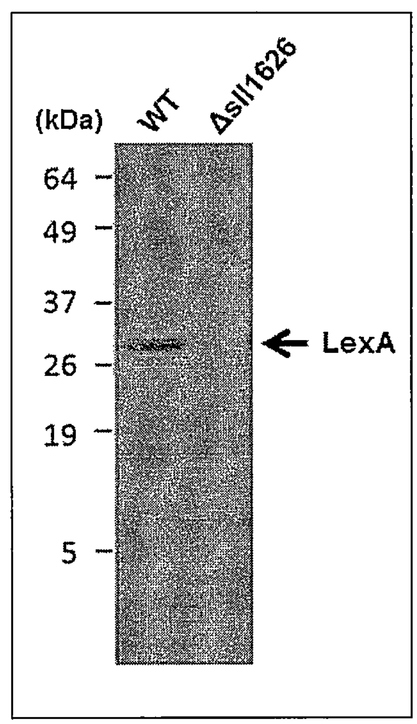

[Figure 2]
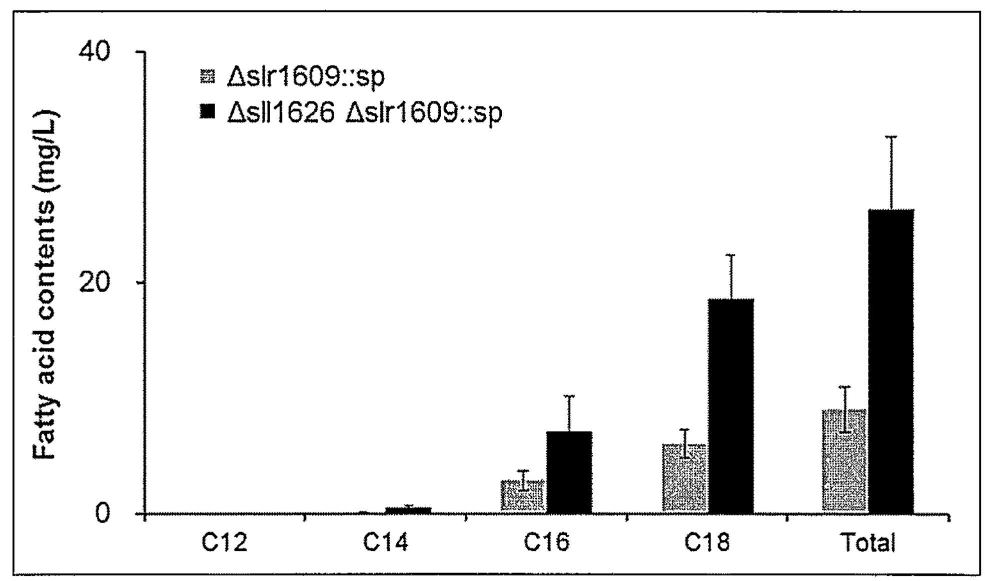
[Figure 3]
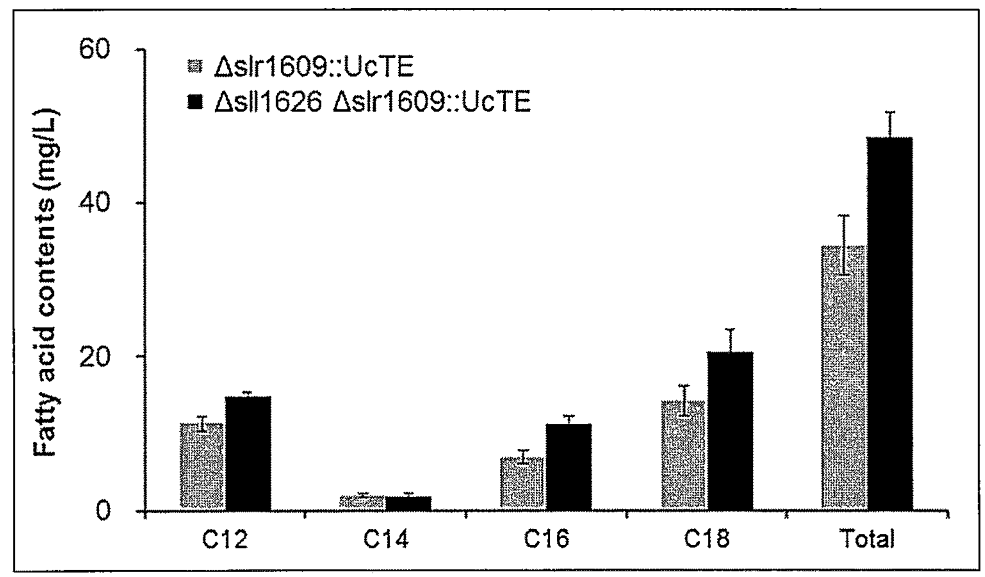

SEQUENCE LISTING

```
<160> NUMBER OF SEQ ID NOS: 25

<210> SEQ ID NO 1
<211> LENGTH: 382
<212> TYPE: PRT
<213> ORGANISM: Umbellularia californica

<400> SEQUENCE: 1

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
```

```
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

<210> SEQ ID NO 2
<211> LENGTH: 1149
<212> TYPE: DNA
<213> ORGANISM: Umbellularia californica

<400> SEQUENCE: 2

```
atggctacca cctctttagc ttccgccttt tgctcgatga aagctgtaat gttagctcgt     60

gatggtcggg gtatgaaacc tcgtagtagt gatttgcaac tccgtgcggg aaatgcgcct    120

acctctttga aaatgatcaa tgggaccaaa ttcagttata cggagagctt gaaacggttg    180

cctgattgga gcatgctctt tgctgttatc accaccatct tttcggctgc tgagaaacaa    240

tggactaatc tagagtggaa gccgaaaccg aagctacccc agttgcttga tgatcatttt    300

ggactgcatg ggttagtttt ccggcgcacc tttgccatcc ggtcttatga agttggacct    360

gatcgctcca cctctattct ggctgttatg aatcatatgc aggaggctac ccttaatcat    420

gcgaaaagtg tgggaattct aggagatgga ttcgggacga cgctagagat gagtaagcgg    480

gatctgatgt gggttgttcg gcgcacgcat gttgctgttg aacggtaccc tacttggggt    540

gatactgtag aagtagagtg ctggattggt gcttctggaa ataatggcat gcgtcgtgat    600

ttccttgtcc gggactgcaa aaccggcgaa attcttactc gctgtaccag cctttcggtg    660

ctgatgaata ctcgcactcg tcgtttgtcc accattcctg atgaagttcg tggtgaaata    720

gggcctgctt tcatcgataa tgttgctgtg aaagacgatg aaattaagaa actacaaaaa    780

ctcaatgata gcactgccga ttatattcaa ggaggtttga cccctcgttg gaatgatttg    840

gatgtcaatc aacatgttaa caacctcaaa tacgttgcct gggtttttga gaccgtcccc    900
```

```
gattccatct ttgagagtca tcatatttcc agcttcactc ttgaatatcg tcgtgagtgt    960

acccgtgata gcgtgctgcg gtccctgacc actgtctctg gtggctcgtc ggaggctggg   1020

ttagtttgcg atcatttgct ccaacttgaa ggtgggtctg aggtattgcg tgccagaact   1080

gagtggcggc ctaaacttac cgatagtttc cgcggcatta gtgttattcc cgccgaaccg   1140

cgcgtgtaa                                                           1149


<210> SEQ ID NO 3
<211> LENGTH: 18
<212> TYPE: DNA
<213> ORGANISM: Artificial Sequence
<220> FEATURE:
<223> OTHER INFORMATION: lexAup-F primer

<400> SEQUENCE: 3

acatttttcg gggtagtc                                                   18


<210> SEQ ID NO 4
<211> LENGTH: 37
<212> TYPE: DNA
<213> ORGANISM: Artificial Sequence
<220> FEATURE:
<223> OTHER INFORMATION: lexAup/km-R primer

<400> SEQUENCE: 4

gaggggatcc tctagagtct ggagaattct cagggtg                              37


<210> SEQ ID NO 5
<211> LENGTH: 32
<212> TYPE: DNA
<213> ORGANISM: Artificial Sequence
<220> FEATURE:
<223> OTHER INFORMATION: Km/lexAdown-F primer

<400> SEQUENCE: 5

ctggagttct tcgcctcagg gtcatgagca at                                   32


<210> SEQ ID NO 6
<211> LENGTH: 18
<212> TYPE: DNA
<213> ORGANISM: Artificial Sequence
<220> FEATURE:
<223> OTHER INFORMATION: lexAdown-R primer

<400> SEQUENCE: 6

cggtgaccac cctagata                                                   18


<210> SEQ ID NO 7
<211> LENGTH: 23
<212> TYPE: DNA
<213> ORGANISM: Artificial Sequence
<220> FEATURE:
<223> OTHER INFORMATION: slr1609f-F primer

<400> SEQUENCE: 7

atggcgctca atccaggata aag                                             23


<210> SEQ ID NO 8
<211> LENGTH: 22
<212> TYPE: DNA
<213> ORGANISM: Artificial Sequence
<220> FEATURE:
<223> OTHER INFORMATION: slr1609r-R primer

<400> SEQUENCE: 8
```

aagtttgggt taccactggt cg 22

<210> SEQ ID NO 9
<211> LENGTH: 21
<212> TYPE: DNA
<213> ORGANISM: Artificial Sequence
<220> FEATURE:
<223> OTHER INFORMATION: slr1609f-R primer

<400> SEQUENCE: 9
tttctaggga gtgccaacag g 21

<210> SEQ ID NO 10
<211> LENGTH: 22
<212> TYPE: DNA
<213> ORGANISM: Artificial Sequence
<220> FEATURE:
<223> OTHER INFORMATION: slr1609r-F primer

<400> SEQUENCE: 10
aacctgagct tgaaccatct cc 22

<210> SEQ ID NO 11
<211> LENGTH: 32
<212> TYPE: DNA
<213> ORGANISM: Artificial Sequence
<220> FEATURE:
<223> OTHER INFORMATION: slr1609/sp-F primer

<400> SEQUENCE: 11
ggcactccct agaaaatcga ttttcgttcg tg 32

<210> SEQ ID NO 12
<211> LENGTH: 34
<212> TYPE: DNA
<213> ORGANISM: Artificial Sequence
<220> FEATURE:
<223> OTHER INFORMATION: slr1609/sp-R primer

<400> SEQUENCE: 12
gttcaagctc aggttcatat gcaagggttt attg 34

<210> SEQ ID NO 13
<211> LENGTH: 22
<212> TYPE: DNA
<213> ORGANISM: Artificial Sequence
<220> FEATURE:
<223> OTHER INFORMATION: slr1609-R primer

<400> SEQUENCE: 13
aacctgagct tgaaccatct cc 22

<210> SEQ ID NO 14
<211> LENGTH: 17
<212> TYPE: DNA
<213> ORGANISM: Artificial Sequence
<220> FEATURE:
<223> OTHER INFORMATION: Sp-F primer

<400> SEQUENCE: 14
atcgattttc gttcgtg 17

<210> SEQ ID NO 15
<211> LENGTH: 37
<212> TYPE: DNA

-continued

<213> ORGANISM: Artificial Sequence
<220> FEATURE:
<223> OTHER INFORMATION: slr1609/psbA2-F primer

<400> SEQUENCE: 15
ggcactccct agaaaattat ttcatctcca ttgtccc 37

<210> SEQ ID NO 16
<211> LENGTH: 40
<212> TYPE: DNA
<213> ORGANISM: Artificial Sequence
<220> FEATURE:
<223> OTHER INFORMATION: psbA2/UcTE-R primer

<400> SEQUENCE: 16
taggaattat aaccataggt tataattcct tatgtatttg 40

<210> SEQ ID NO 17
<211> LENGTH: 23
<212> TYPE: DNA
<213> ORGANISM: Artificial Sequence
<220> FEATURE:
<223> OTHER INFORMATION: UcTE-F primer

<400> SEQUENCE: 17
atggctacca cctctttagc ttc 23

<210> SEQ ID NO 18
<211> LENGTH: 34
<212> TYPE: DNA
<213> ORGANISM: Artificial Sequence
<220> FEATURE:
<223> OTHER INFORMATION: UcTE/sp-R primer

<400> SEQUENCE: 18
gaacgaaaat cgatttacac gcgcggttcg gcgg 34

<210> SEQ ID NO 19
<211> LENGTH: 423
<212> TYPE: DNA
<213> ORGANISM: Synechocystis sp. PCC6803

<400> SEQUENCE: 19
acatttttcg ggtagtctc aattttgctt tttcgccctc aatcacagcg gcgatcgcct 60
tctgctggcc gaaaatgagg aaccgtcgga agaaatgtaa aattttgtat cttttttagt 120
atgattgccc tgaatgttat gactgggttt aaaatagtcc tagagtccta aatacattcc 180
tataggagat attacatgga acctctcacc cgagcccaaa aagaactttt tgactggtta 240
gttagttaca ttgacgaaac ccagcacgcc ccctccatcc gccaaatgat gcgggccatg 300
aatttgcgtt ctccggcccc cattcaaagt cgattggaac ggttacgcaa taagggttac 360
gttgattgga ctgacggcaa agcccgcacc ctgagaattc tccagactct agaggatccc 420
ctc 423

<210> SEQ ID NO 20
<211> LENGTH: 409
<212> TYPE: DNA
<213> ORGANISM: Synechocystis sp. PCC6803

<400> SEQUENCE: 20
ctggagttct tcgcctcagg gtcatgagca atgacctcgt ggacgatttt attgtcgaag 60
gtgatatgct gattctccgt tctgtgactg gagaagagga aatcgaagat ggggaattgg 120

```
tcgccgccag tattaagggg ggcaagattg ctatcaaacg ctattaccaa gatggcacta    180

aggtcgtact caaagcctcc aacaacaaag gccctggcca agaattgaaa gccagcgatg    240

ttgaaatcca ggggatttta atgggggttt ggcgcaattt ccagggagtt tagcccggca    300

ttaccgggaa cagctcaaaa accacactgg taaaactttt tacttctatc cctaggctgg    360

cgatcgcctt tcgctggcct gtttttatgg ctatctaggg tggtcaccg                409


<210> SEQ ID NO 21
<211> LENGTH: 1158
<212> TYPE: DNA
<213> ORGANISM: Enterococcus faecalis

<400> SEQUENCE: 21

atcgattttc gttcgtgaat acatgttata ataactataa ctaataacgt aacgtgactg     60

gcaagagata tttttaaaac aatgaatagg tttacactta ctttagtttt atggaaatga    120

aagatcatat catatataat ctagaataaa attaactaaa ataattatta tctagataaa    180

aaatttagaa gccaatgaaa tctataaata aactaaatta agtttattta attaacaact    240

atggatataa aataggtact aatcaaaata gtgaggagga tatatttgaa tacatacgaa    300

caaattaata aagtgaaaaa aatacttcgg aaacatttaa aaaataacct tattggtact    360

tacatgtttg gatcaggagt tgagagtgga ctaaaaccaa atagtgatct tgacttttta    420

gtcgtcgtat ctgaaccatt gacagatcaa agtaaagaaa tacttataca aaaaattaga    480

cctatttcaa aaaaaatagg agataaaagc aacttacgat atattgaatt aacaattatt    540

attcagcaag aaatggtacc gtggaatcat cctcccaaac aagaatttat ttatggagaa    600

tggttacaag agctttatga acaaggatac attcctcaga aggaattaaa ttcagattta    660

accataatgc tttaccaagc aaaacgaaaa aataaaagaa tatacggaaa ttatgactta    720

gaggaattac tacctgatat tccattttct gatgtgagaa gagccattat ggattcgtca    780

gaggaattaa tagataatta tcaggatgat gaaaccaact ctatattaac tttatgccgt    840

atgattttaa ctatggacac gggtaaaatc ataccaaaag atattgcggg aaatgcagtg    900

gctgaatctt ctccattaga acatagggag agaattttgt tagcagttcg tagttatctt    960

ggagagaata ttgaatggac taatgaaaat gtaaatttaa ctataaacta tttaaataac   1020

agattaaaaa aattataaaa aaattgaaaa aatggtggaa acactttttt caattttttt   1080

gttttattat ttaatatttg ggaaatattc attctaattg gtaatcagat tttagaaaac   1140

aataaaccct tgcatatg                                                 1158


<210> SEQ ID NO 22
<211> LENGTH: 295
<212> TYPE: DNA
<213> ORGANISM: Synechocystis sp. PCC6803

<400> SEQUENCE: 22

attatttcat ctccattgtc cctgaaaatc agttgtgtcg cccctctaca cagcccagaa     60

ctatggtaaa ggcgcacgaa aaaccgccag gtaaactctt ctcaaccccc aaaacgccct    120

ctgtttaccc atggaaaaaa cgacaattac aagaaagtaa aacttatgtc atctataagc    180

ttcgtgtata ttaacttcct gttacaaagc tttacaaaac tctcattaat cctttagact    240

aagtttagtc agttccaatc tgaacatcga caaatacata aggaattata accat         295


<210> SEQ ID NO 23
```

```
<211> LENGTH: 20
<212> TYPE: DNA
<213> ORGANISM: Escherichia coli

<400> SEQUENCE: 23

tactgtatat atatacagta                                                20


<210> SEQ ID NO 24
<211> LENGTH: 14
<212> TYPE: DNA
<213> ORGANISM: Anabaena sp.
<220> FEATURE:
<221> NAME/KEY: misc_feature
<222> LOCATION: (6)..(8)
<223> OTHER INFORMATION: n can be any nucleotide

<400> SEQUENCE: 24

rgtacnnndg twcb                                                      14


<210> SEQ ID NO 25
<211> LENGTH: 14
<212> TYPE: DNA
<213> ORGANISM: Nostoc sp.
<220> FEATURE:
<221> NAME/KEY: misc_feature
<222> LOCATION: (7)..(7)
<223> OTHER INFORMATION: n can be any nucleotide

<400> SEQUENCE: 25

agtacwnwtg tact                                                      14
```

MODIFIED CYANOBACTERIA

REFERENCE TO SEQUENCE LISTING SUBMITTED ELECTRONICALLY

The content of the electronically submitted substitute sequence listing, file name 2537_1350001_SeqListing.txt, size 12,472 bytes; and date of creation Oct. 18, 2017, filed herewith, is incorporated herein by reference in its entirety.

FIELD OF THE INVENTION

The present invention relates to modified cyanobacteria improved in fatty acid secretory productivity.

BACKGROUND OF THE INVENTION

Recently, it has been predicted that fossil fuels will be depleted in future. In order to solve energy problems, it is an urgent issue to establish technologies for producing next-generation energy alterative to fossil fuels. As one of them, a technology for biofuel production using photosynthetic organisms such as cyanobacteria and algae has attracted attention and been researched. The photosynthetic organisms can produce biofuels from carbon, which was photosynthetically fixed from $CO_2$ and water using light as an energy source. In addition, the photosynthetic organisms are not competitive with food raw materials and can realize carbon-neutral fuel production. Because of these advantages, the photosynthetic organisms are expected as a next-generation energy production system.

Cyanobacteria (also called blue-green algae) belong to a group of eubacteria and have an ability to fix $CO_2$ and produce oxygen through photosynthesis. Cyanobacteria, which have an outer membrane and a cell wall formed of peptidoglycan, fall into the category of gram-negative bacteria but are phylogenetically far from typical gram-negative bacteria. Over a billion years ago, cyanobacteria were engulfed by eukaryotic cells. Such intracellular symbiont (primary symbiosis), cyanobacteria, are considered as an origin of chloroplasts and thus have been widely used in photosynthesis studies as an ancestor organism of chloroplasts.

Cyanobacteria grow fast and have a high photosynthetic ability as well as a transformation ability. Because of this, cyanobacterial cells, to which foreign DNA is introduced, can be used in microbiological production of substances and thus have attracted attention as a microbial host for producing a biofuel. As examples of biofuels produced by cyanobacteria, hydrogen (Non Patent Literature 1), ethanol (Non Patent Literature 2), isobutanol (Non Patent Literature 3) and fatty acids (Non Patent Literature 4) are reported. Non Patent Literature 4 and Patent Literature 1 describe a method for converting inorganic carbon to a fatty acid by culturing a recombinant cyanobacterial cell producing exogenic acyl-ACP thioesterase.

(Patent Literature 1) JP-A-2011-505838

(Non Patent Literature 1) Yoshino F. et al. (2007) Mar. Biotechnol. 9: 101-112

(Non Patent Literature 2) Deng M. D. and Coleman J. R. (1999) Appl. Environ. Microbiol. 65: 523-528

(Non Patent Literature 3) Atsumi S. et al. (2009) Nat. Biotechnol. 27: 1177-1180

(Non Patent Literature 4) Liu X. et al. (2011) Proc. Natl. Acad. Sci. USA. 108: 6899-6904

SUMMARY OF THE INVENTION

In an aspect, the present invention provides a method for producing a modified cyanobacterium, comprising causing a loss of function of a transcriptional regulator LexA and acyl-ACP synthetase in a cyanobacterium.

In another aspect, the present invention provides a method for improving productivity of a fatty acid secreted from a cyanobacterium, comprising causing loss of function of a transcriptional regulator LexA and acyl-ACP synthetase in the cyanobacterium.

In a further another aspect, the present invention provides a modified cyanobacterium which has lost the functions of a transcriptional regulator LexA and acyl-ACP synthetase.

In furthermore aspect, the present invention provides a method for producing a fatty acid, comprising culturing the modified cyanobacterium as mentioned above and a modified cyanobacterium produced by the aforementioned method.

BRIEF DESCRIPTION OF THE DRAWINGS

FIG. 1 The figure shows the results of western blotting of LexA protein in a wild-type strain (WT) and a transcriptional regulator LexA knockout strain (Δsll1626).

FIG. 2 The figure is a graph showing the amount of free fatty acid in a broth of each of Δslr1609::sp strain and Δsll1626Δslr1609::sp strain (n=3, error bar=SD).

FIG. 3 The figure is a graph showing the amount of free fatty acid in a broth of each of Δslr1609::UcTE strain and Δsll1626Δslr1609::UcTE strain (n=3, error bar=SD).

DETAILED DESCRIPTION OF THE INVENTION

1. Definition

In the specification, nucleotide sequence identity and amino acid sequence identity are calculated in accordance with the Lipman-Pearson method (Science, 1985, 227: 1435-1441). To be more specific, by using genetic information processing software, Genetyx-Win homology (Search homology) analysis program, nucleotide sequence identity and amino acid sequence identity are calculated by assuming that the unit size to compare (ktup) is specified as 2.

In the specification, the concept of "loss" of function or "lost" function includes partial loss of function (more specifically, reduction, suppression or partial inhibition of function) and complete loss of function. For example, in the specification, "loss of function of a transcriptional regulator LexA" may mean that the function of the regulator decreases. In the specification, "loss of function of acyl-ACP synthetase" may mean that the acyl-ACP synthetic activity of the enzyme decreases or is completely lost. For example, "loss of function of a transcriptional regulator LexA or acyl-ACP synthetase in a cyanobacterium" may refer to lowering the expression level of the regulator or the enzyme, thereby decreasing LexA transcriptional regulatory function or acyl-ACP synthetic activity in a cyanobacterium; or refer to deleting a gene encoding the regulator or the enzyme.

Cyanobacteria, also called as blue-green algae, belong to a group of prokaryotes performing photosynthesis using their chlorophylls. Cyanobacteria are highly diversified. In view of cell morphology, there are unicellular cyanobacteria, such as *Synechocystis* sp. PCC6803, filamentous cyanobacteria formed of many cells connected like a string, such as *Anabaena* sp. PCC7120, performing nitrogen fixation and forming heterocysts, and spiral and branched cyanobacteria. In view of growth environment, there are cyanobacteria species adapted in various conditions including thermophilic cyanobacteria such as *ThermoSynechococcus elongatus*

BP-1 isolated from Beppu Onsen; and oceanic cyanobacteria such as *Synechococcus* sp. CC9311 living in the coast or *Synechococcus* sp. WH8102 living in the outer sea. As cyanobacteria having feature intrinsic to the species, *Microcystis aeruginosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are also mentioned.

In cyanobacteria, carbon dioxide fixed by photosynthesis is converted into acetyl-CoA via a large number of enzymatic reaction processes. In the initial stage of fatty acid synthesis, malonyl-CoA is synthesized from acetyl-CoA and $CO_2$ by the function of acetyl-CoA carboxylase. Next, malonyl-CoA is converted into malonyl-ACP by the function of malonyl CoA:ACP transacylase. Thereafter, while fatty acid synthetase (or acyl-ACP synthetase) progressively works, two carbon units are sequentially added to synthesize acyl-ACP, which are increased in two carbons and used as an intermediate for synthesizing e.g., a membrane fatty acid.

The transcriptional regulator LexA (hereinafter sometimes simply referred to as LexA) is a protein characterized by a helix-turn-helix structure DNA binding domain (pfam01726) at the N terminal side and a Peptidase_S24-like sequence (pfam00717) at the C terminal side and known as a transcription factor playing an important role in regulating gene expression. The transcriptional regulator LexA is widely distributed in gram-positive bacteria and gram-negative bacteria. For example, it is reported that, in *Escherichia coli*, LexA recognizes an SOS-box sequence (TACTGTATATATATACAGTA; SEQ ID NO: 23) and binds it to suppress transcription of genes belonging to SOS regulon and involved in regulating DNA repair and cellular division. More specifically, it is reported as follows: when genomic DNA is damaged, LexA itself is degraded by the autoprotease activity; due to the inactivation of DNA binding capacity of LexA by its degradation, suppression of genes by LexA is released, and as a result, SOS regulon gene is expressed to activate DNA repair capacity and induce mutation (Friedberg, E. C. et al., DNA Repair and Mutagenesis, American Society of Microbiology Press, 2005, 463-508).

LexA has been conserved in many cyanobacterial species. Information concerning cyanobacterial species having LexA or LexA of each cyanobacterial species is available from, for example, CyanoBase ([genome.microbedb.jp/cyanobase/]) or NCBI database ([www.ncbi.nlm.nih.gov/genome/] or [www.ncbi.nlm.nih.gov/protein/]). For example, *Synechocystis* sp. PCC6803 of the genus *Synechocystis* mentioned above has sll1626 gene as a gene encoding LexA. Also, genes SYNPCC7002_A1849 and SYNW1582 of the genus *Synechococcus*, genes P9303_19141 and PMT0380 of the genus *Prochlorococcus*, gene AM1_3948 of the genus *Acaryochloris*, genes cce_1899, cce_5074 and PCC8801_2186 of the genus *Cyanothece* and genes alr4908 and all3272 of the genus *Anabaena* are all genes encoding LexA.

In contrast, it is reported that some LexA of cyanobacteria functions differently from LexA of e.g., *Escherichia coli*. For example, it is reported that sll1626 gene encoding LexA of *Synechocystis* sp. PCC6803 is known to be an essential gene for growth; however, the protein encoded by the sll1626 gene is not involved in expression control of SOS regulon for e.g., DNA repair, different from LexA of e.g., *Escherichia coli*. (Mol Microbiol, 2004, 53 (1): 65-80). Furthermore, it is also reported that LexA of *Synechocystis* sp. PCC6803 accelerates expression of hox operon (hoxEFUYH) encoding bidirectional hydrogenase involved in hydrogen generation under light irradiation conditions (Mol Microbiol, 2005, 58 (3): 810-823). Besides these reports, a gene encoding LexA itself and redox-sensitive RNA helicase, crhR (Nucleic Acids Res, 2006, 34 (12): 3446-354) are reported as genes whose expressions are inhibited by LexA of *Synechocystis* sp. PCC6803. As a sequence recognizing LexA of *Synechocystis* sp. PCC6803, for example, a sequence containing 12 nucleotides of "CTA-N9-CTA" is reported (FEBS Lett, 2008, 582 (16): 2424-30). In contrast, LexA of *Anabaena* sp. PCC7120 is reported that it accelerates expression of bidirectional hydrogenase similarly to PCC6803 strain mentioned above and recognizes a pseudo-palindrome sequence, RGTACNNNDGTWCB (SEQ ID NO: 24) (Mol Genet Genomics, 2004, 271 (1): 40-9). Furthermore, a palindrome sequence of approximately 14 bp represented by AGTACWNWTGTACT (SEQ ID NO: 25) is reported as a putative recognition sequence of LexA of cyanobacteria (BMC Genomics, 2010, 11: 527).

Accordingly, in the specification, "transcriptional regulator LexA" in cyanobacteria refers to, in a broad sense, a protein having an amino acid sequence having a helix-turn-helix structure at the N terminal side and identified as a DNA binding domain (pfam01726) and an amino acid sequence identified as Peptidase_S24-like sequence (pfam00717) at the C-terminal side and having a function of controlling transcription of a gene. In practice, the transcriptional regulator LexA can be identified by search based on homology with a known LexA gene by use of BLAST (blast.ncbi.nlm.nih.gov/Blast.cgi?CMD=Web&PAGE_TYPE=Blast Home). In the specification, the phrase: "polypeptide having a structure and function as a transcriptional regulator LexA" means that the polypeptide has a structure having a helix-turn-helix serving as a DNA binding domain at the N terminal side and a Peptidase_S24-like sequence at the C terminal side, and having a function of controlling gene transcription.

Information concerning genes and proteins of cyanobacteria is open to public, for example, in the aforementioned CyanoBase and the NCBI database. Those skilled in the art can obtain the amino acid sequence of a desired protein (for example, transcriptional regulator LexA or acyl-ACP synthetase) of a cyanobacterium or the nucleotide sequences of a gene encoding of the protein based on information of these database.

2. Modified Cyanobacterium

Various techniques for producing biofuels from carbon (raw material) of atmospheric $CO_2$ depending upon cyanobacterium photosynthesis have been developed; however, their productivity is still low. In the context, there has been demanded to develop a more highly efficient technique for producing biofuel. The present invention relates to providing cyanobacteria improved in fatty acid productivity.

The present inventors prepared a modified cyanobacterium by causing loss of function of transcriptional regulator LexA and acyl-ACP synthetase in a cyanobacterium or by further introducing a gene encoding acyl-ACP thioesterase in the cyanobacterium. As a result, they found that the quantity of fatty acid secretory production per broth of the cyanobacterium or bacterial cell increases in the modified cyanobacterium.

According to the present invention, it is possible to obtain a modified cyanobacterium improved in fatty acid secretory productivity. An efficient microbiological production of fatty acid becomes possible by culturing the modified cyanobacterium of the present invention.

The present invention provides a modified cyanobacterium improved in fatty acid secretory productivity. The modified cyanobacterium of the present invention is a cyanobacterium modified by causing loss of function of a transcriptional regulator LexA and acyl-ACP synthetase.

The type of cyanobacterium (hereinafter sometimes referred to as a parent cyanobacterium) serving as a parent microorganism of the modified cyanobacterium of the present invention, in other words, the type of cyanobacterium before modified by causing loss of function of transcriptional regulator LexA and acyl-ACP synthetase is not particularly limited. Any type of cyanobacterium can be used as a parent cyanobacterium. Examples of the parent cyanobacterium are preferably cyanobacteria belonging to *Synechocystis, Synechococcus, Prochlorococcus, Acaryochloris, Cyanothece* and *Anabaena*; more preferably, cyanobacteria belonging to *Synechocystis, Synechococcus* and *Anabaena*; further preferably, *Synechocystis* sp. PCC6803, *Synechocystis* sp. PCC7509, *Synechocystis* sp. PCC6714, *Synechococcus* sp. PCC7002, *Synechococcus* sp. WH8102, *Prochlorococcus* sp. MIT9303, *Prochlorococcus marinus* MIT9313, *Acaryochloris marina* MBIC11017, *Cyanothece* sp. ATCC51142, *Cyanothece* sp. PCC8801, and *Anabaena* sp. PCC7120; and further more preferably, *Synechocystis* sp. PCC6803, *Synechocystis* sp. PCC6714 and *Synechocystis* sp. PCC7509; and still further preferably *Synechocystis* sp. PCC6803.

The amino acid sequence of LexA transcriptional regulator of a parent cyanobacterium, a gene encoding the amino acid sequence, the position of the gene on the genome or a plasmid, and the nucleotide sequence of the gene can be checked on the aforementioned CyanoBase and NCBI database. For example, as a preferable example of the transcriptional regulator LexA whose function is to be lost from a parent cyanobacterium in the present invention, LexA encoded by the following genes will be described: sll1626 of *Synechocystis* sp. PCC6803, SYNPCC7002_A1849 of *Synechococcus* sp. PCC7002, SYNW1582 of *Synechococcus* sp. WH8102, P9303_19141 of *Prochlorococcus* sp. MIT9303, PMT0380 of *Prochlorococcus marinus* MIT9313, AM1_3948 of *Acaryochloris marina* MBIC11017, cce_1899 or cce_5074 of *Cyanothece* sp. ATCC51142, PC08801_2186 of *Cyanothece* sp. PCC8801 or alr4908 or all3272 of *Anabaena* sp. PCC7120. Alternatively, as the LexA, the function of which is to be lost in the present invention, a polypeptide having the amino acid sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the amino acid sequences of LexA mentioned above; and having a structure and function as a transcriptional regulator LexA, can be mentioned.

The amino acid sequence of the acyl-ACP synthetase of a cyanobacterium and a gene encoding the amino acid sequence, the position of the gene and the nucleotide sequence thereof can be checked on the aforementioned CyanoBase and NCBI database. In the present invention, preferable examples of the acyl-ACP synthetase, the function of which is to be lost from a parent cyanobacterium, include Slr1609 of *Synechocystis* sp. PCC6803, SYNPCC7002_A0675 of *Synechococcus* sp. PCC7002, SYNW0669 of *Synechococcus* sp. WH8102, P9303_21391 of *Prochlorococcus sp. MIT*9303, PMT0215 of *Prochlorococcus marinus MIT*9313, AM1_5562 and AM1_2147 of *Acaryochloris marina* MBIC11017, CCE_1133 of *Cyanothece* sp. ATCC51142, PCC8801_0332 of *Cyanothece* sp. PCC8801, and Alr3602 of *Anabaena* sp. PCC7120. Alternatively, the acyl-ACP synthetase, the function of which is to be lost in the present invention, a polypeptide having the amino acid sequence having an identity of 40% or more, preferably 50% or more, more preferably 60% or more, further preferably 70% or more, further more preferably 80% or more, still further preferably 90% or more, still further more preferably 95% or more with any one of the amino acid sequences of acyl-ACP synthetase proteins mentioned above, and having a function of synthesizing acyl-ACP, can be mentioned.

A means for causing loss of function of the LexA transcriptional regulator or acyl-ACP synthetase in cyanobacteria is not particularly limited as long as it is usually used in causing loss of function of proteins. For example, deleting and inactivating a gene encoding LexA or acyl-ACP synthetase; introducing a mutation which decreases activity of or inactivates the protein to be expressed to the gene; introducing a mutation which inhibits transcription of the gene; inhibiting translation of a transcript of the gene; or administering an inhibitor specifically inhibiting a desired protein expressed, may be mentioned. Among these, it is preferable to delete or inactivate a gene encoding a transcriptional regulator LexA and a gene encoding acyl-ACP synthetase in the cyanobacterium.

In the present invention, examples of the gene encoding a transcriptional regulator LexA, which is to be deleted or inactivated in order to cause loss of function of the transcriptional regulator LexA, include sll1626 of *Synechocystis* sp. PCC6803, SYNPCC7002_A1849 of *Synechocystis* sp. PCC7002, SYNW1582 of *Synechococcus* sp. WH8102, P9303_19141 of *Prochlorococcus* sp. MIT9303, PMT0380 of *Prochlorococcus marinus* MIT9313, AM1_3948 of *Acaryochloris marina* MBIC11017, cce_1899 and cce_5074 of *Cyanothece* sp. ATCC51142, PCC8801_2186 of *Cyanothece* sp. PCC8801, and alr4908 and all3272 of *Anabaena* sp. PCC7120, as mentioned above. These genes and nucleotide sequences can be checked on the aforementioned CyanoBase or NCBI database. For example, a polynucleotide encoding Sll1626 of *Synechocystis* sp. PCC6803 can be identified as sll1626 gene (NCBI Gene ID: 954404); and a polynucleotide encoding SYNPCC7002_A1849 of *Synechocystis* sp. PCC7002 can be identified as SYNPCC7002_A1849 gene (NCBI Gene ID: 6,057,790). Furthermore, a polynucleotide having a nucleotide sequence having an identify of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of these genes, and encoding a polypeptide having a structure and function as a LexA transcriptional regulator can be mentioned as an example of the gene encoding a transcriptional regulator LexA to be deleted or inactivated in the present invention.

In the present invention, as a preferable example of the gene encoding a transcriptional regulator LexA to be deleted or inactivated, sll1626 gene and a polynucleotide consisting of a nucleotide sequence having an identity of 80% or more, preferably 90% or more, more preferably 95% or more, further preferably 98% or more, and still further preferably 99% or more with the nucleotide sequence of sll1626 gene, and encoding a polypeptide having a structure and function as a transcriptional regulator LexA can be mentioned.

As an example of the gene encoding acyl-ACP synthetase to be deleted or inactivated in order to cause loss of function in the present invention, polynucleotides encoding the following proteins can be mentioned: Slr1609 of *Synechocystis* sp. PCC6803, SYNPCC7002_A0675 of *Synechococcus* sp. PCC7002, SYNW0669 of *Synechococcus* sp. WH8102, P9303_21391 of *Prochlorococcus* sp. MIT9303, PMT0215 of *Prochlorococcus marinus* MIT9313, AM1_5562 or AM1_2147 of *Acaryochloris marina* MBIC11017, CCE_1133 of *Cyanothece* sp. ATCC51142, PCC8801_0332 of *Cyanothece* sp. PCC8801 or Alr3602 of *Anabaena* sp. PCC7120. These genes and nucleotide sequences thereof can be checked on the aforementioned CyanoBase or NCBI database. For example, a polynucleotide encoding Slr1609 of *Synechocystis* sp. PCC6803 can be identified as slr1609 gene (NCBI Gene ID: 953643); a polynucleotide encoding SYNPCC7002_A0675 of *Synechococcus* sp. PCC7002 as SYNPCC7002_A0675 gene (NCBI Gene ID: 6057029); a polynucleotide encoding SYNW0669 of *Synechococcus* sp. WH8102 as SYNW0669 gene (NCBI-Gene ID: 1730682); and a polynucleotide encoding Alr3602 of *Anabaena* sp. PCC7120 as alr3602 gene. Furthermore, a polynucleotide having a nucleotide sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of these genes, and encoding a polypeptide having a function of synthesizing acyl-ACP, can be mentioned as an example of the gene encoding acyl-ACP synthetase to be deleted or inactivated in the present invention.

Preferable examples of the gene encoding acyl-ACP synthetase to be deleted or inactivated in the present invention include slr1609 gene, SYNPCC7002_A0675 gene and a polynucleotide consisting of a nucleotide sequence having an identity of 80% or more, preferably 90% or more, more preferably 95% or more, further preferably 98% or more, and still further preferably 99% or more with the nucleotide sequence of slr1609 gene or SYNPCC7002_A0675 gene, and encoding a polypeptide having a function of synthesizing acyl-ACP. More preferable example is slr1609 gene.

As means for deleting or inactivating the gene as mentioned above, introduction of a mutation of one or more nucleotides in the nucleotide sequence of the gene, substitution or insertion of a different nucleotide sequence in the nucleotide sequence, or deletion of a part or whole sequence of the gene, is mentioned. As a means for introducing a mutation which decreases the activity of or inactivates a protein expressed to a gene, introducing a mutation to the gene such that a site involved in activity of a protein encoded by the gene varies is mentioned. As means for introducing a mutation which inhibits transcription of the gene as mentioned above, introduction of a mutation in a promoter region of the gene and inactivation of the promotor by substitution or insertion of a different nucleotide sequence, are mentioned. Examples of a specific method for introducing a mutation and for substituting or inserting a nucleotide sequence may include ultraviolet irradiation and site-specific mutagenesis, homologous recombination and SOE (splicing by overlap extension)-PCR method (Gene, 1989, 77: 61-68). As means for inhibiting the translation of a transcript as mentioned above, interference of RNA by micro RNA can be mentioned. As a protein-specific inhibitor, a specific antibody against the protein, its receptor or ligand can be mentioned.

In a preferable embodiment, the modified cyanobacterium of the present invention may further have an introduction of a heterologous gene encoding acyl-ACP thioesterase in addition to the aforementioned modification. In other words, the modified cyanobacterium according to a preferable embodiment of the present invention may be a cyanobacterium in which functions of LexA transcriptional regulator and acyl-ACP synthetase are functionally lost and which further have a heterologous gene encoding acyl-ACP thioesterase. The acyl-ACP thioesterase is an enzyme of dissociating a fatty acid chain from acyl-ACP in the fatty acid synthesis pathway. It is reported that if acyl-ACP thioesterase is introduced in a cyanobacterium, a fatty acid is cleaved out from acyl-ACP produced by fatty acid synthesis to produce a free fatty acid (Non Patent Literature 4). In another report, it is pointed out that in order to efficiently secrete a free fatty acid produced by the function of acyl-ACP thioesterase in a cyanobacterium, it is effective to cause functional loss of endogenous acyl-ACP synthetase gene (Plant Physiol, 2010, 152: 1598-1610). Accordingly, if a gene encoding acyl-ACP thioesterase is externally introduced to the modified cyanobacterium of the present invention, production of a fatty acid within the cell is promoted and secretory production of fatty acid by the modified cyanobacterium can be further improved.

As the gene encoding acyl-ACP thioesterase to be introduced into the modified cyanobacterium of the present invention, genes isolated from e.g., plants containing a large amount of medium-chain fatty acids in seed oil or algae capable of producing fatty acids can be mentioned. For example, a gene encoding acyl-ACP thioesterase derived from the following plant or alga is mentioned: *Arabidopsis thaliana; Bradyrhizobium japonicum; Brassica napus; Cinnamonum camphorum; Capsicum chinense; Cuphea hookeriana; Cuphea lanceolata; Cuphea palustris; Coriandrum sativum* L.; *Carthamus tinctorius; Cuphea wrightii; Elaeis guineensis; Gossypium hirsutum; Garcinia mangostana; Helianthus annuus; Iris germanica; Iris tectorum; Myristica fragrans; Triticum aestivum; Ulmus Americana; Cinnamomum camphorum; Cocos nucifera*; or *Umbellularia californica*. Alternatively, a gene encoding acyl-ACP thioesterase of *Escherichia coli* can be introduced into the modified cyanobacterium of the present invention. The heterologous gene encoding acyl-ACP thioesterase of the present invention is preferably a gene encoding acyl-ACP thioesterase (NCBI database GI: 595955) derived from *Umbellularia californica*, a gene encoding acyl-ACP thioesterase (GI: AAC49151.1) of *Cinnamomum camphorum*, a gene encoding acyl-ACP thioesterase (GI: AEM72521.1) of *Cocos nucifera* or a gene encoding acyl-ACP thioesterase (GI: AAC73596.1) of *Escherichia coli*. The genes encoding acyl-ACP thioesterase derived from the above plants, algae or *Escherichia coli* can be identified on the NCBI database. For example, acyl-ACP thioesterase (UcTE) gene derived from *Umbellularia californica* has been registered as GenBank ID: U17097 in the NCBI database. Furthermore, for example, genes encoding acyl-ACP thioesterase of *Cinnamomum camphorum* and *Cocos nucifera* have been registered as GenBank ID: U31813 and GenBank ID: JF338905, respectively. Moreover, for example, a gene encoding acyl-ACP thioesterase of *E. coli* K-12 strain has been registered as NCBI Gene ID: 945127.

Preferable examples of the acyl-ACP thioesterase gene to be introduced into a cyanobacterium in the present invention may include a gene encoding acyl-ACP thioesterase UcTE derived from *Umbellularia californica* consisting of the amino acid sequence represented by SEQ ID NO: 1 and a gene encoding a polypeptide consisting of an amino acid sequence having an identity of 80% or more, preferably 90% or more, more preferably 95% or more, further preferably 98% or more, and still further preferably 99% or more with the amino acid sequence of UcTE represented by SEQ ID NO: 1, and having a function of dissociating a fatty acid chain from acyl-ACP.

Acyl-ACP thioesterase has a specificity to the fatty acid chain length and degree of unsaturation of a substrate, acyl-ACP (U.S. Pat. No. 5,298,421, Planta, 1993, 189: 425-432). Accordingly, a free fatty acid having a desired chain length and unsaturation degree can be produced by a cyanobacterium by changing the type of acyl ACP thioesterase to be introduced. For example, the acyl-ACP thioesterase (UcTE) derived from *Umbellularia californica*, as mentioned above has a substrate specificity to a C12 (chain-length) acyl group and mainly produces a C12 (chain length) free fatty acid such as lauric acid (C12: 0). For example, the acyl-ACP thioesterases of *Cinnamomum camphorum* and *Cocos nucifera*, as mentioned above have a substrate specificity to a C14 (chain length) acyl group and mainly produce a C14 (chain length) free fatty acid such as myristic acid (C14: 0). For example, the acyl-ACP thioesterase of *E. coli* K-12 strain as mentioned above has a substrate specificity to a C16 or C18 (chain length) acyl group and mainly produces a C16 or C18 (chain-length) free fatty acid such as palmitic acid (C16: 0), palmitoleic acid (016: 1), stearic acid (C18: 0), oleic acid (C18: 1), linoleic acid (C18: 2) and linolenic acid (C18: 3).

The heterogeneous acyl-ACP thioesterase gene to be introduced into the modified cyanobacterium of the present invention is preferably optimized in codon in accordance with use frequency of codon in the cyanobacterium. Information concerning codons used in each of organisms is available from Codon Usage Database ([www.kazusa.or.jp/codon/]). Examples of the acyl-ACP thioesterase gene, the codon of which has been optimized for a cyanobacterium may include a polynucleotide encoding UcTE (SEQ ID NO: 1) having the nucleotide sequence represented by SEQ ID NO: 2 and a polynucleotide encoding a polypeptide or having a nucleotide sequence having an identity of 80% or more, preferably 90% or more, more preferably 95% or more, further preferably 98% or more and still further preferably 99% or more with the nucleotide sequence represented by SEQ ID NO: 2, and having a function of dissociating a fatty acid chain from acyl-ACP.

In introducing a heterogeneous acyl-ACP thioesterase gene into a cyanobacterium, for example, a vector such as a plasmid vector can be used. As the vector, an expression vector is preferable. For example, an expression vector containing a DNA fragment of a heterogeneous acyl-ACP thioesterase gene and a promoter for expressing the gene is constructed. As the promoter, a lac, tac or trc promoter, a promotor which is induced by addition of isopropyl β-D-1-thiogalactopyranoside (IPTG) or a promotor, which is involved in expression of, for example, Rubisco operon (rbc), a gene (psaAB) encoding a PSI reaction-center protein or a gene (psbA) encoding D1 protein of PSII reaction-center and isolated from cyanobacterium, can be used; however, the promotor is not limited to these and various types of promoters which function in cyanobacteria can be used. Furthermore, in the above expression vectors, a marker gene (for example, a gene resistant to a drug such as kanamycin, chloramphenicol, spectinomycin or erythromycin) is further integrated therein for selecting a host having the vector properly introduced therein. The expression vector as mentioned above is introduced into a parent cyanobacterium or the modified cyanobacterium of the present invention by known means to transform the cyanobacterium. As a method for introducing the vector into a cyanobacterium, a general method such as a natural transformation method, an electroporation method and a conjugation method can be used. A cyanobacterium transformed is cultured in a selection medium, for example, an antibiotic-containing medium, to successfully obtain transformants having the desired trait.

In a preferable embodiment, a heterogeneous acyl-ACP thioesterase gene is introduced in the region of an endogenous acyl-ACP synthetase gene on the genome of a cyanobacterium. In this way, acyl-ACP synthetase in the cyanobacterium is functionally lost; at the same time, an ability to express heterogeneous acyl-ACP thioesterase is provided. For example, a DNA fragment of a heterogeneous acyl-ACP thioesterase gene with a DNA fragment of the acyl-ACP synthetase gene region added to both ends is constructed by the SOE-PCR method (Gene, 1989, 77: 61-68) and introduced into a vector. The vector is introduced into a cyanobacterium to cause homologous recombination on the genome with the acyl-ACP synthetase gene region. In this manner, a modified cyanobacterium having the heterogeneous acyl-ACP thioesterase gene introduced in the acyl-ACP synthetase gene region on the genome, can be obtained. In another embodiment, a heterogeneous acyl-ACP thioesterase gene may be introduced into a region (neutral site) of the genome of a cyanobacterium where any gene, if introduced, will not damage the cyanobacterium.

3. Method for Producing Fatty Acid

The modified cyanobacterium of the present invention can be produced in the aforementioned procedure. The modified cyanobacterium of the present invention is improved in fatty acid secretory productivity. Accordingly, if the modified cyanobacterium of the present invention is cultured in suitable conditions and then, the fatty acid secreted there is recovered, a microbiological fatty acid can be efficiently produced. The fatty acids which are secreted and produced by cyanobacteria in accordance with the fatty acid production method of the present invention may be free fatty acids, preferably a free fatty acid rich in lauric acid (C12: 0).

Cyanobacteria can be generally cultured based on a liquid culture using a BG-11 medium (J Gen Microbiol, 1979, 111: 1-61) or a modified method. The culture for producing a fatty acid may be performed in a period during which bacterial cells are sufficiently grown to accumulate fatty acids in high concentrations, for example, from 7 to 45 days, preferably from 10 to 30 days, and more preferably from 14 to 21 days, by an aeration/spinner culture or shaking culture.

By the above culture, a cyanobacterium produces a fatty acid and secretes the fatty acid in the culture. The fatty acid secreted may be recovered by removing a solid content such as cells from the culture by filtration and/or centrifugation, collecting the remaining liquid component, recovering or purifying the fatty acid by e.g., a chloroform/methanol extraction method, a hexane extraction method or an ethanol extraction method. In a large-scale production, the fatty acid can be recovered by collecting an oil content from the culture from which cells are removed, by squeezing or extraction, and subjecting the oil content to general purification such as degumming, deacidification, bleaching, dewaxing and deodorization. In the fatty acid production method of the present invention, since a fatty acid is secreted outside the cyanobacterial cells, it is not necessary to destroy the cells for recovering the fatty acid. The remaining cells after the fatty acid is recovered can be repeatedly used for fatty acid production.

The fatty acid obtained by the fatty acid production method using the modified cyanobacterium of the present invention can be used not only as foods but also as raw materials for emulsifiers which are blended in e.g., cosmetics, cleaning agents such as soaps or detergents, fiber treatment agents, hair rinses or disinfectants and preservatives.

4. Exemplary Embodiments

As other exemplary embodiments of the present invention mentioned above, the following compositions, production methods, uses or methods will be disclosed in the specification; however, the present invention is not limited by these embodiments.

<1> A method for producing a modified cyanobacterium, comprising causing loss of function of a transcriptional regulator LexA and acyl-ACP synthetase in a cyanobacterium.

<2> A method for improving fatty acid secretory productivity in a cyanobacterium, comprising causing loss of function of a transcriptional regulator LexA and acyl-ACP synthetase in the cyanobacterium.

<3> A modified cyanobacterium which has lost the functions of transcriptional regulator LexA and acyl-ACP synthetase.

<4> The method according to <1>, preferably comprising deleting or inactivating a gene encoding a transcriptional regulator LexA and a gene encoding acyl-ACP synthetase in the cyanobacterium.

<5> The method according to <2>, preferably comprising deleting or inactivating a gene encoding a transcriptional regulator LexA and a gene encoding acyl-ACP synthetase in the cyanobacterium.

<6> The modified cyanobacterium according to <3>, preferably comprising deleting or inactivating a gene encoding a transcriptional regulator LexA and a gene encoding acyl-ACP synthetase.

<7> The method according to <1> or <4>, preferably further comprising introducing a heterologous gene encoding acyl-ACP thioesterase.

<8> The method according to <2> or <5>, preferably further comprising introducing a heterologous gene encoding acyl-ACP thioesterase.

<9> The modified cyanobacterium according to <3> or <6>, preferably comprising a heterologous gene encoding acyl-ACP thioesterase.

<10> In any one of <4> to <9>, the gene encoding the transcriptional regulator LexA is preferably selected from the group consisting of following (1) and (2):

(1) a gene selected from the group consisting of sll1626, SYNPCC7002_A1849, SYNW1582, P9303_19141, PMT0380, AM1_3948, cce_1899, cce_5074, PCC8801_2186, alr4908 and all3272; and (2) a polynucleotide having a nucleotide sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of genes shown in (1) above, and encoding a polypeptide having a structure and function as a transcriptional regulator LexA.

<11> In any one of <4> to <10>, the gene encoding acyl-ACP synthetase is preferably selected from the group consisting of the following (1) and (2):

(1) a polynucleotide encoding a protein selected from the group consisting of Slr1609, SYNPCC7002_A0675, SYNW0669, P9303_21391, PMT0215, AM1_5562, AM1_2147, CCE_1133, PCC8801_0332 and Alr3602; and (2) a polynucleotide having a nucleotide sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of the polynucleotides shown in (1) above, and encoding a polypeptide having a function of synthesizing acyl-ACP.

<12> In any one of <7> to <11>, preferably, the heterologous gene encoding acyl-ACP thioesterase is selected from the group consisting of the following (1) to (4):

(1) a gene encoding a polypeptide consisting of the amino acid sequence represented by SEQ ID NO: 1; and (2) a gene encoding a polypeptide consisting of the amino acid sequence having an identity of 80% or more preferably 90% or more, more preferably 95% or more, further preferably 98% or more, and still further preferably 99% or more with the amino acid sequence represented by SEQ ID NO: 1, and having a function of dissociating a fatty acid chain from acyl-ACP;

(3) a polynucleotide consisting of the nucleotide sequence represented by SEQ ID NO: 2; and (4) a polynucleotide having a nucleotide sequence having an identity of 80% or more, preferably 90% or more, more preferably 95% or more, further preferably 98% or more and still further preferably 99% or more with the nucleotide sequence represented by SEQ ID NO: 2 and encoding a polypeptide having a function of dissociating a fatty acid chain from acyl-ACP.

<13> In any one of <7> to <11>, preferably, the heterologous gene encoding acyl-ACP thioesterase is a gene encoding acyl-ACP thioesterase of *Cinnamomum camphorum* or *Cocos nucifera.*

<14> In any one of <7> to <11>, preferably, the heterologous gene encoding acyl-ACP thioesterase is a gene encoding acyl-ACP thioesterase of *Escherichia coli* K-12.

<15> In any one of <7> to <14>, preferably, the heterologous gene encoding acyl-ACP thioesterase is introduced in the region of the gene encoding acyl-ACP synthetase or a neutral site in the genome sequence of the cyanobacterium.

<16> In any one of <1> to <15>, the cyanobacterium is preferably a cyanobacterium of *Synechocystis, Synechococcus, Prochlorococcus, Acaryochloris, Cyanothece* or *Anabaena;* more preferably, *Synechocystis* sp. PCC6803, *Synechocystis* sp. PCC7509, *Synechocystis* sp. PCC6714, *Synechococcus* sp. PCC7002, *Synechococcus* sp. WH8102, *Prochlorococcus* sp. MIT9303, *Prochlorococcus marinus* MIT9313, *Acaryochloris marina* MBIC11017, *Cyanothece* sp. ATCC51142, *Cyanothece* sp. PCC8801 or *Anabaena* sp. PCC7120.

<17> A method for producing a fatty acid, comprising culturing the modified cyanobacterium produced by the method according to any one of the above <1>, <4>, <7> and <10> to <16>, or the modified cyanobacterium according to any one of <3>, <6>, <9> and <10> to <16>.

<18> The method according to <17>, in which preferably, a gene encoding acyl-ACP thioesterase derived from *Umbel-*

*lularia californica* is introduced in the modified cyanobacterium and C12 (chain length) free fatty acid is mainly produced.

<19> The method according to <17>, in which preferably, a gene encoding acyl-ACP thioesterase derived from *Cinnamomum camphorum* or *Cocos nucifera* is introduced in the modified cyanobacterium and C14 (chain length) free fatty acid is mainly produced.

<20> The method according to <17>, in which preferably, a gene encoding acyl-ACP thioesterase derived from *Escherichia coli* K-12 is introduced in the modified cyanobacterium and C16 or C18 (chain length) free fatty acid is mainly produced.

EXAMPLE

Now, the present invention will be more specifically described based on Examples; however, the present invention is not limited to these.

Example 1 Construction of a Transcriptional Regulator LexA/acyl-ACP Synthetase Double Knockout Modified Cyanobacterial Strain (1) Construction of Transcriptional Regulator LexA Knockout Strain In *Synechocystis* sp. PCC6803, which is a unicellular and photoheterotrophic cyanobacterium, a gene for a transcriptional regulator LexA, sll1626 was deleted. Using the genomic DNA of *Synechocystis* sp. PCC6803 wild-type strain as a template and primer sets shown in Table 1, a fragment upstream of sll1626 (SEQ ID NO: 19) and a fragment downstream of sll1626 (SEQ ID NO: 20) were amplified. These PCR products and a fragment of a kanamycin resistance marker gene (cleaved from pRL161 plasmid by HincII treatment), i.e., three fragments, were mixed to prepare a DNA solution. Using the DNA solution as a template, fusion PCR was carried out to obtain a lexA knockout construct, Δsll1626:: Km fragment. *Synechocystis* sp. PCC6803 strain was transformed with the Δsll1626:: Km fragment. A transcriptional regulator LexA knockout strain (Δsll1626 strain) was obtained by screening based on kanamycin resistance.

TABLE 1

| Primer | Sequence | SEQ ID NO: |
|---|---|---|
| lexAup-F | 5'-ACATTTTTCGGGGTAGTC-3 | 3 |
| lexAup/km-R | 5'-GAGGGGATCCTCTAGAGTCTGGAGAATT CTCAGGGTG-3' | 4 |
| Km/lexAdown-F | 5'-CTGGAGTTCTTCGCCTCAGGGTCATGAG CAAT-3' | 5 |
| lexAdown-R | 5'-CGGTGACCACCCTAGATA-3' | 6 |

(2) Verification of LexA Expression Level of Transcriptional Regulator LexA Knockout Strain The LexA expression level in Δsll1626 strain constructed in the above (1) was checked. Cyanobacteria were cultured in a 50 mL of BG-11 medium placed in a 50 mL-large test tube under constant illumination (50 $\mu E \cdot m^{-2} \cdot sec^{-1}$) while supplying sterile air at 30° C. Wild-type strain and Δsll1626 strain cultured were centrifuged to remove the culture supernatant. The resultant bacterial cells were each suspended in a grinding buffer (50 mM Tris-HCl (pH7.5), 50 mM NaCl). To the suspension, zirconia beads were added to grind bacterial cells. In this manner, a solution containing a protein derived from the bacterial cells was obtained. A solution containing a protein corresponding to $1.0 \times 10^7$ cells was taken out per sample and subjected to SDS-PAGE. LexA protein was detected by western blot analysis.

In the western blot analysis, first, to the protein solution obtained, 1×sample buffer (62.5 mM Tris-HCl (pH6.8), 5% 2-mercaptoethanol, 2% SDS, 5% sucrose, 0.002% Bromophenol blue) was solubilized. After 15% SDS-PAGE was carried out, blotting was carried out on PVDF (polyvinyl difluoride membrane: Immobilon; 0.45 μm pore size; Millipore). As a primary antibody, an anti-His-LexA polyclonal antibody was used. As a secondary antibody, an HRP-labeled anti-rabbit IgG antibody (Biorad) was used. Thereafter, light was allowed to emit by using EzWestLumi plus (ATTO) and expose to an X-ray film. In this manner, a band derived from LexA was detected.

As a result, a LexA band was found with respect to the wild-type strain, as shown in FIG. 1; whereas, a band derived from LexA was virtually not found with respect to the LexA knockout strain (Δsll1626 strain), which demonstrates that the amount of LexA protein was remarkably low. From the results, it was verified that the function of the transcriptional regulator LexA decreases in the LexA knockout Δsll1626 strain.

(3) Construction of Transcriptional Regulator LexA/acyl-ACP Synthetase Double Knockout Strain Secretory production of a fatty acid by *Synechocystis* sp. PCC6803 in a broth can be attained by causing loss of function of endogenous acyl-ACP synthetase (Slr1609) (Plant Physiol, 2010, 152: 1598-1610). It was reported that fatty acid production is promoted by introducing a gene encoding acyl-ACP thioesterase into PCC6803 strain (Non Patent Literature 4). In this example, a spectinomycin resistant gene was inserted in the coding region of slr1609 gene encoding acyl-ACP synthetase on the genome of Δsll1626 strain to inactivate the slr1609 gene. In this manner, the function of acyl-ACP synthetase was lost to prepare a modified strain improved in fatty acid production. Furthermore, an acyl-ACP thioesterase (UcTE) gene derived from *Umbellularia californica* (codon was optimized in accordance with *Synechocystis* sp. PCC6803) was inserted into the slr1609 coding region to prepare a modified strain further improved in fatty acid productivity. A method for preparing the modified strain will be more specifically described below.

From genome DNA of *Synechocystis* sp. PCC6803 wild-type strain, a partial gene fragment of slr1609 (2049 bp) was amplified using primers slr1609f-F and slr1609r-R shown in Table 2, and cloned at the HincII site in pUC118 plasmid (manufactured by Takara Bio Inc.) to obtain pUC118-slr1609 plasmid.

PCR using pDG1726 plasmid (Guerout-Fleury et al., Gene, 1995, 167: 335-336) as a template and primers slr1609/sp-F and slr1609/sp-R shown in Table 2, was carried out to obtain a spectinomycin resistant marker gene fragment (sp fragment: SEQ ID NO: 21). Next, PCR using the pUC118-slr1609 plasmid as a template and primers slr1609f-R and slr1609r-F shown in Table 2, was carried out to obtain a linear DNA fragment having a deletion of 242 bp-region in slr1609 gene coding region. This fragment was ligated to the sp fragment by In-Fusion (registered trade mark) PCR cloning method (Clontech) to obtain pUC118-slr1609::sp plasmid containing a DNA sequence of slr1609 gene coding region having the sp fragment inserted therein.

PCR using the pUC118-slr1609::sp plasmid as a template and primers slr1609f-R and Sp-F shown in Table 2, was carried out to obtain a linear plasmid. Using primers slr1609/psbA2-F and psbA2/UcTE-R shown in Table 2, a promoter region fragment (SEQ ID NO: 22) of psbA2 gene derived from *Synechocystis* sp. PCC6803 was amplified by PCR. The acyl-ACP thioesterase (UcTE) gene fragment (UcTE fragment: SEQ ID NO: 2) derived from *Umbellularia californica* was prepared by artificially synthesizing a sequence, the codon of which was optimized in accordance with *Synechocystis* sp. PCC6803, described in Non Patent Literature 4, and amplifying the sequence by PCR using primers of UcTE-F and UcTE/sp-R shown in Table 2. Next, to the linear plasmid obtained above, the psbA2 promoter region fragment and the UcTE fragment were cloned by In-Fusion (registered trade mark) PCR cloning method (Clontech) to obtain pUC118-slr1609::psbA2-UcTE-sp plasmid having an insertion, which consists of the psbA2 promoter region fragment, UcTE fragment and sp fragment arranged in this order, in the slr1609 gene coding region.

The *Synechocystis* sp. PCC6803 wild-type strain was transformed with the resultant pUC118-slr1609::sp plasmid and selected based on spectinomycin resistance to obtain Δslr1609::sp strain in which acyl-ACP synthetase gene slr1609 on the genome was inactivated.

Furthermore, another *Synechocystis* sp. PCC6803 wild-type strain was transformed with the resultant pUC118-slr1609::psbA2-UcTE-sp plasmid and selected based on spectinomycin resistance. In this manner, Δslr1609::UcTE strain in which acyl-ACP synthetase gene slr1609 was inactivated; at the same time, acyl-ACP thioesterase expressional potency was provided, was obtained by introducing the acyl-ACP thioesterase (UcTE) gene (codon optimized) in the acyl-ACP synthetase slr1609 gene coding region on the genome.

The Δsll1626 strain prepared in the above (1) was further transformed with pUC118-slr1609:: sp plasmid. A transformant was selected based on spectinomycin resistance to obtain Δsll1626Δslr1609:: sp strain, in which LexA gene, sll1626, and acyl-ACP synthetase gene, slr1609, on the genome were inactivated.

Another Δsll1626 strain prepared in the above (1) was further transformed with pUC118-slr1609:: psbA2-UcTE-sp plasmid. A transformant was selected based on spectinomycin resistance. In this manner, LexA gene, sll1626 on the genome was inactivated. Further, a codon-optimized acyl-ACP thioesterase (UcTE) gene was introduced in the code region of acyl-ACP synthetase gene, slr1609 to obtain Δsll1626Δslr1609:: UcTE strain in which acyl-ACP synthetase gene, slr1609, was inactivated and acyl-ACP thioesterase expression potency was provided.

TABLE 2

| Primer | Sequence | SEQ ID NO: |
|---|---|---|
| slr1609f-F | 5'-ATGGCGCTCAATCCAGGATAAAG-3' | 7 |
| slr1609r-R | 5'-AAGTTTGGGTTACCACTGGTCG-3' | 8 |
| slr1609f-R | 5'-TTTCTAGGGAGTGCCAACAGG-3' | 9 |
| slr1609r-F | 5'-AACCTGAGCTTGAACCATCTCC-3 | 10 |
| slr1609/sp-F | 5'-GGCACTCCCTAGAAAATCGATTTTCGT TCGTG-3' | 11 |

TABLE 2 -continued

| Primer | Sequence | SEQ ID NO: |
|---|---|---|
| slr1609/sp-R | 5.-GTTCAAGCTCAGGTTCATATGCAAGGG TTTATTG-3' | 12 |
| slr1609-R | 5'-AACCTGAGCTTGAACCATCTCC-3' | 13 |
| Sp-F | 5'-ATCGATTTTCGTTCGTG-3' | 14 |
| slr1609/psbA2-F | 5'-GGCACTCCCTAGAAAATTATTTCATCT CCATTGTCCC-3' | 15 |
| psbA2/UcTE-R | 5'-TAGGAATTATAACCATAGGTTATAATT CCTTATGTATTTG-3' | 16 |
| UcTE-F | 5'-ATGGCTACCACCTCTTTAGCTTC-3' | 17 |
| UcTE/sp-R | 5'-GAACGAAAATCGATTTACACGCGCGGT TCGGCGG-3' | 18 |

Example 2 Improvement of Fatty Acid Secretory Productivity of Modified Cyanobacterial Strain (1) Culture of Modified Strain A modified cyanobacterium strain produced in Example 1 was cultured and productivity of a fatty acid secreted therefrom was checked. The cyanobacterium was cultured in 25-mL BG-11 medium placed in a 50 mL Erlenmeyer flask at an initial cell density ($OD_{730}$) of 0.2, under constant illumination (60 $\mu E \cdot m^{-2} \cdot sec^{-1}$) at 30° C. by use of a rotary shaker (120 rpm). In the conditions, Δslr1609:: sp strain, Δsll1626Δslr1609:: sp strain, Δslr1609:: UcTE strain and Δsll1626Δslr1609:: UcTE strain were individually cultured for two weeks.

(2) Analysis of Fatty Acid Composition

After completion of the culture, to each of the broths (50 mL), 1 g of $NaHPO_4$ and 50 μL of 7-pentadecanone (1 mg/mL) dissolved in methanol used as the internal standard were added. To this broth, hexane (10 mL) was added. The mixture was sufficiently stirred, allowed to stand still for 10 minutes and centrifuged at room temperature and 2500 rpm for 10 minutes. Then, the upper layer was taken and placed in an eggplant flask, concentrated under reduced pressure and centrifuged. To the resultant lower layer, hexane (5 mL) was further added. The mixture was stirred and centrifuged. This operation was repeated twice to obtain a dry sample. To the dry sample, a 5% hydrochloric acid methanol solution (3 mL) was added and the mixture was treated at a constant temperature of 80° C. for 3 hours. In this manner, methyl esterification of a fatty acid was carried out. Thereafter, hexane (3 mL) was added. The mixture was sufficiently stirred and allowed to stand still for 5 minutes. The upper layer was taken, appropriately concentrated and subjected to gas chromatographic analysis. The measurement conditions are shown below. [capillary column:DB-1 MS 30 m×200 μm×0.25 μm (J&W Scientific), mobile phase: highly pure helium, flow rate within column: 1.0 mL/minute, temperature raising program: 100° C. (1 minute)→10° C./minute→300° C. (5 minutes), equilibration time:1 minute, inlet: split injection (split ratio: 100: 1), pressure 14.49 psi, 104 mL/minute, injection volume 1 μL, wash vial: methanol/chloroform, detector's temperature: 300° C.]

Based on the peak area of the waveform (data) obtained by the gas chromatographic analysis, the amount of each fatty acid methyl ester was quantified. Note that, each of the peak areas was compared to the peak area of the internal standard, i.e., 7-pentadecanone, to correct difference between the samples. The amounts of fatty acids contained in a broth (1 liter) and the total amount thereof were calculated.

The results are shown in FIGS. 2 and 3 and Table 3. Note that, the values shown in FIGS. 2 and 3 and Table 3 are average values of the results of cultures independently carried out three times and chromatographic analysis. As is apparent from FIG. 2, the production amounts of individual free fatty acids increased and the total amount of free fatty acids greatly increased in Δsll1626Δslr1609:: sp strain, in which LexA gene, sll1626 and acyl ACP synthetase gene, slr1609 were knocked out, compared to Δslr1609:: sp strain having intact LexA gene. As is apparent from FIG. 3, the production amounts of individual free fatty acids and the total free fatty acid production amount greatly increased in Δsll1626Δslr1609:: UcTE strain, in which LexA gene sll1626 and acyl ACP synthetase gene slr1609 were knocked out and thioesterase UcTE gene was introduced, compared to Δslr1609:: UcTE strain having intact LexA gene. More specifically, as shown in Table 3, in culture for two weeks, Δsll1626Δslr1609:: sp strain exhibited the total fatty acid production amount 2.92 times as large as that of Δslr1609:: sp strain; and Δsll1626Δslr1609:: UcTE strain exhibited the total fatty acid production amount 1.41 times as large as that of Δslr1609:: UcTE strain. Further, the fatty acid production amount of Δsll1626Δslr1609:: UcTE strain in which thioesterase UcTE was introduced was 1.84 times as large as that of Δsll1626Δslr1609:: sp strain having no acyl-ACP thioesterase gene introduced therein. The production amount of C12 fatty acid in the UcTE gene-introduced strain greatly increased compared to that of a strain having no UcTE gene introduced therein.

TABLE 3

| | Free fatty acid production amount [mg/L; Mean ± SD] | | | | |
|---|---|---|---|---|---|
| Modified strain | C12 | C14 | C16 | C18 | Total |
| Δslr1609::sp | 0.00 ± 0.00 | 0.04 ± 0.08 | 2.90 ± 0.82 | 6.09 ± 1.23 | 9.03 ± 1.96 |
| Δsll1626Δslr1609::sp | 0.00 ± 0.00 | 0.47 ± 0.22 | 7.18 ± 2.99 | 18.70 ± 3.69 | 26.35 ± 6.28 |
| (vs. Δslr1609::sp) | | | | | (291.8%) |
| Δslr1609::UcTE | 11.34 ± 0.96 | 2.00 ± 0.22 | 6.97 ± 0.89 | 14.20 ± 2.00 | 34.52 ± 3.89 |
| Δsll1626Δslr1609::UcTE | 14.91 ± 0.52 | 1.93 ± 0.36 | 11.14 ± 1.13 | 20.54 ± 2.87 | 48.53 ± 3.24 |
| (vs. Δslr1609::UcTE) | | | | | (140.6%) |
| (vs. Δsll1626Δslr1609::sp) | | | | | (184.1%) |

The invention claimed is:

1. A method for producing a modified cyanobacterium, comprising deleting or inactivating the cyanobacterium's transcriptional regulator LexA and acyl-ACP synthetase genes, wherein the cyanobacterium is a member of the *Synechocystis* sp., *Synechococcus* sp. or *Anabaena* sp., and wherein the total amount of C12 to C18 free fatty acids that is produced by the modified cyanobacterium is greater than that produced by the unmodified cyanobacterium.

2. The method according to claim 1, comprising inactivating a gene encoding transcriptional regulator LexA and a gene encoding acyl-ACP synthetase in the cyanobacterium.

3. The method according to claim 1, wherein the gene encoding transcriptional regulator LexA is a gene selected from the group consisting of the *Synechocystis* sp. PCC6803 sll1626 gene, the *Synechococcus* sp. SYNPCC7002_A1849 gene, the *Synechococcus* sp. SYNW1582 gene, the *Anabaena* sp. alr4908 gene, and the *Anabaena* sp. all3272 gene.

4. The method according to claim 1, wherein the gene encoding acyl-ACP synthetase is a gene selected from the group consisting of the *Synechocystis* sp. PCC6803 slr1609 gene, the *Synechococcus* sp. PCC7002 SYNPCC7002_A0675 gene, the *Synechococcus* sp. WH8102 SYNW0669 gene, and the *Anabaena* sp. PCC7120 alr3602 gene.

5. The method according to claim 1, further comprising introducing a heterologous gene encoding acyl-ACP thioesterase into the cyanobacterium.

6. The method according to claim 5, wherein the gene encoding acyl-ACP thioesterase is a gene encoding a polypeptide consisting of the amino acid sequence of SEQ ID NO: 1 or an amino acid sequence having an identity of 90% or more therewith.

7. The method according to claim 5, wherein the gene encoding acyl-ACP thioesterase is introduced into a region of the gene encoding acyl-ACP synthetase.

8. The method according to claim 1, wherein the cyanobacterium belongs to *Synechocystis*.

9. A method for improving fatty acid secretory productivity in a cyanobacterium, comprising deleting or inactivating the cyanobacterium's transcriptional regulator LexA and acyl-ACP synthetase genes, wherein the cyanobacterium is a member of the *Synechocystis* sp., *Synechococcus* sp. or *Anabaena* sp. and wherein the total amount of C12 to C18 free fatty acids that is produced by the modified cyanobacterium is greater than that produced by the unmodified cyanobacterium.

10. The method according to claim 9, comprising inactivating a gene encoding transcriptional regulator LexA and a gene encoding acyl-ACP synthetase in the cyanobacterium.

11. The method according to claim 9, wherein the gene encoding transcriptional regulator LexA is a gene selected from the group consisting of the *Synechocystis* sp. PCC6803 sll1626 gene, the *Synechococcus* sp. SYNPCC7002_A1849 gene, the *Synechococcus* sp. SYNW1582 gene, the *Anabaena* sp. alr4908 gene, and the *Anabaena* sp. all3272 gene.

12. The method according to claim 9, wherein the gene encoding acyl-ACP synthetase is a gene selected from the group consisting of the *Synechocystis* sp. PCC6803 slr1609 gene, the *Synechococcus* sp. PCC7002 SYNPCC7002_A0675 gene, the *Synechococcus* sp. WH8102 SYNW0669 gene, and the *Anabaena* sp. PCC7120 alr3602 gene.

13. The method according to claim 9, further comprising introducing a heterologous gene encoding acyl-ACP thioesterase into the cyanobacterium.

14. The method according to claim 13, wherein the gene encoding acyl-ACP thioesterase is a gene encoding a polypeptide consisting of the amino acid sequence of SEQ ID NO:1 or an amino acid sequence having an identity of 90% or more therewith.

15. The method according to claim 13, wherein the gene encoding acyl-ACP thioesterase is introduced into a region of the gene encoding acyl-ACP synthetase.

16. The method according to claim 9, wherein the cyanobacterium belongs to *Synechocystis*.

17. A method for producing a fatty acid, comprising culturing the modified cyanobacterium produced by the method according to claim 1.

18. The method according to claim 1, comprising deleting a gene encoding transcriptional regulator LexA and a gene encoding acyl-ACP synthetase in the cyanobacterium.

19. The method according to claim 9, comprising deleting a gene encoding transcriptional regulator LexA and a gene encoding acyl-ACP synthetase in the cyanobacterium.

* * * * *